United States Patent
Peyrl et al.

(10) Patent No.: US 11,389,366 B2
(45) Date of Patent: Jul. 19, 2022

(54) MEASURING METHOD AND APPARATUS FOR DETERMINING THE LENGTH CONDITIONS, THE POSITION AND/OR THE RADIUS OF MOVEMENT OF THE LOWER EXTREMITIES OF A BED-BOUND PATIENT

(71) Applicant: REACTIVE ROBOTICS GMBH, Munich (DE)

(72) Inventors: Helfried Peyrl, Oberhaching (DE); Oliver Zillig, Munich (DE); Kathleen Jones, Munich (DE); Philipp Metzner, Freising (DE)

(73) Assignee: ReActive Robotics GmbH, Munich (DE)

( * ) Notice: Subject to any disclaimer, the term of this patent is extended or adjusted under 35 U.S.C. 154(b) by 268 days.

(21) Appl. No.: 16/625,843

(22) PCT Filed: Jun. 27, 2018

(86) PCT No.: PCT/DE2018/100587
§ 371 (c)(1),
(2) Date: Dec. 23, 2019

(87) PCT Pub. No.: WO2019/001636
PCT Pub. Date: Jan. 3, 2019

(65) Prior Publication Data
US 2020/0121540 A1    Apr. 23, 2020

(30) Foreign Application Priority Data
Jun. 27, 2017 (DE) .................. 10 2017 114 290

(51) Int. Cl.
*A61H 1/02*     (2006.01)
*A61B 5/107*    (2006.01)
*A61B 5/11*     (2006.01)

(52) U.S. Cl.
CPC ......... *A61H 1/0255* (2013.01); *A61B 5/1071* (2013.01); *A61B 5/1122* (2013.01);
(Continued)

(58) Field of Classification Search
CPC .......... A61H 1/00; A61H 1/02; A61H 1/0214; A61H 1/0218; A61H 1/0229;
(Continued)

(56) References Cited

U.S. PATENT DOCUMENTS

| | | | |
|---|---|---|---|
| 6,685,658 B1 * | 2/2004 | Dietz ............... | A61H 1/0229 128/845 |
| 10,842,705 B2 * | 11/2020 | Sampson ............ | A61H 1/024 |

(Continued)

FOREIGN PATENT DOCUMENTS

| | | |
|---|---|---|
| CN | 106621207 A | 5/2017 |
| DE | 8514240 U1 | 10/1985 |

(Continued)

*Primary Examiner* — Valerie L Woodward
*Assistant Examiner* — Paige Kathleen Bugg
(74) *Attorney, Agent, or Firm* — Laurence A. Greenberg; Werner H. Stemer; Ralph E. Locher

(57) ABSTRACT

A measuring method determines the length conditions, the position and/or the radius of movement of the lower extremities of a bed-bound patient. A knee module of a rehabilitation mechanism is connected to a point of application of a leg of the patient. A measuring device records and determines a trajectory solely of the point of application during a movement of the leg by the knee module. A model generation device creates a kinematic model from the data. This allows a determination of the length conditions, the position and/or the radius of movement during an initializing movement without having to undertake any surgical intervention. This does away with the need for complex sensor technology and provides a kinematic model of the radius of movement of the patient, the parameters of which kinematic (Continued)

model are used for establishing new therapeutic procedures within the patient's physical therapy.

18 Claims, 8 Drawing Sheets

(52) U.S. Cl.
CPC .......... *A61H 1/024* (2013.01); *A61B 2505/09* (2013.01); *A61H 2001/0203* (2013.01); *A61H 2201/1207* (2013.01); *A61H 2201/165* (2013.01); *A61H 2201/1642* (2013.01); *A61H 2201/5007* (2013.01); *A61H 2201/5058* (2013.01); *A61H 2201/5061* (2013.01); *A61H 2201/5064* (2013.01); *A61H 2201/5069* (2013.01); *A61H 2205/088* (2013.01); *A61H 2205/102* (2013.01)

(58) Field of Classification Search
CPC .... A61H 1/0237; A61H 1/024; A61H 1/0244; A61H 1/0255; A61H 1/0259; A61H 1/0262; A61H 3/00–068; A61H 2003/001–065; A61F 2/605; A61F 2/206; A61F 2/64; A61F 5/0123; A61F 5/0102; A61F 5/0127; A61F 5/01–0109; A61F 5/012–0125; A61F 2005/0132–0179; B25J 9/0006; A61B 5/1071; A61B 5/1122; A61B 5/1072; A61B 5/4836; A61B 5/6828; A61B 5/6892; A61B 2505/09; A61B 2503/08; G09B 19/003; G09B 23/28; A63B 22/06–0694; A63B 2022/0611–0688; A63B 24/0003; A63B 24/0006; A63B 24/0021; A63B 24/0075; A63B 2024/0009; A63B 2024/0012; A63B 2024/0015; A63B 2024/0068; A63B 2024/0075

USPC ................. 434/247, 255–258, 262, 267, 274
See application file for complete search history.

(56) References Cited

U.S. PATENT DOCUMENTS

| | | | |
|---|---|---|---|
| 2007/0282228 A1* | 12/2007 | Einav | A63B 21/00178 601/33 |
| 2009/0124939 A1* | 5/2009 | Hansenberger | A61H 23/0254 601/46 |
| 2010/0222716 A1* | 9/2010 | Olsen | A61H 1/00 601/26 |
| 2012/0253235 A1* | 10/2012 | Pellis | A61B 5/1071 600/595 |
| 2012/0330198 A1* | 12/2012 | Patoglu | B25J 9/0006 601/33 |
| 2013/0072821 A1* | 3/2013 | Odermatt | A61B 34/25 600/595 |
| 2015/0352394 A1* | 12/2015 | Marti | A61B 5/6835 482/139 |
| 2018/0085276 A1* | 3/2018 | Brodard | A61N 1/0484 |
| 2018/0303696 A1 | 10/2018 | Koenig et al. | |

FOREIGN PATENT DOCUMENTS

| | | | | |
|---|---|---|---|---|
| DE | 10060466 | A1 | 6/2002 | |
| DE | 102014105250 | A1 * | 10/2015 | ......... A63B 21/4034 |
| DE | 102015117596 | B3 | 8/2016 | |
| JP | H10258101 | A | 9/1998 | |
| JP | H1176329 | A | 3/1999 | |
| JP | 2003225264 | A | 8/2003 | |
| JP | 2005334385 | A | 12/2005 | |
| WO | 0061059 | A1 | 10/2000 | |
| WO | 2015127396 | A1 | 8/2015 | |
| WO | 2017063639 | A1 | 4/2017 | |

* cited by examiner

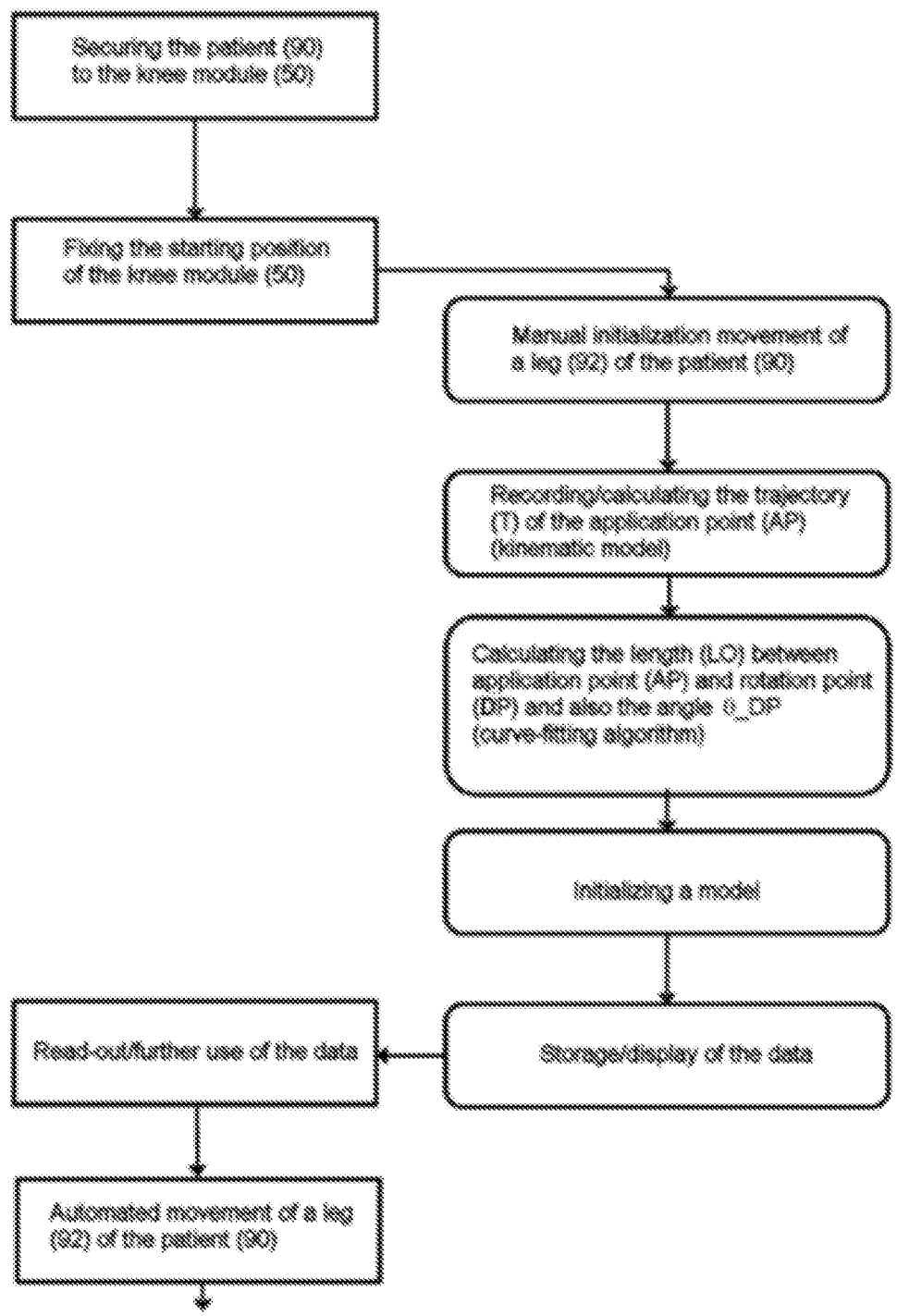

MEASURING METHOD AND APPARATUS FOR DETERMINING THE LENGTH CONDITIONS, THE POSITION AND/OR THE RADIUS OF MOVEMENT OF THE LOWER EXTREMITIES OF A BED-BOUND PATIENT

BACKGROUND OF THE INVENTION

Field of the Invention

The present invention relates to a measuring method for determining the length conditions, the position and/or the radius of movement of the lower extremities of a bedridden patient, such as hip joint, knee joint and/or upper leg, and to an apparatus for carrying out such a method, at least comprising a rehabilitation mechanism with at least one knee module which can be operatively connected to the knee joint of a patient and which comprises at least one electric motor for driving at least two eccentrics.

Bedridden patients (understood hereinbelow in particular as patients who whether conscious or unconscious are unable, for medical reasons, to get out of bed by themselves for any length of time) have been shown to profit from regular physiotherapy.

During long phases of confinement to bed, physiotherapy exercises, which the patient in most cases performs with the assistance of persons specially trained in physiotherapy, can maintain the mobility and muscle mass of the patient, promote the circulation of blood through the body and thus reduce the risk of clotting, for example.

In the case of bedridden patients who are unconscious, kinesitherapy of the lower extremities has in particular proven effective since, by movement of the legs, large muscle groups of the body can be trained and thus a greater stimulus can be triggered for the patient's brain. Physiotherapy exercises can thus even accelerate healing of damaged regions of the brain and can facilitate waking from a coma.

However, factors mitigating against the widespread medical use of kinesitherapy include the considerable costs in terms of personnel and the associated financial burden placed on hospitals, which costs are often unable to be met within the legal framework of the healthcare system. For coma patients in particular, the exercises are then carried out too infrequently and are of too short a duration.

For this reason, attempts have been made in recent years to increasingly automate the kinesitherapy of bedridden patients, which is traditionally carried out manually by physiotherapists.

The documents JP 2005 334385 A, JP H10 258101 A, WO 00/61059 A1, JP 2003 225264 A, and also the document WO 2017/063639 A1 from the applicant, disclose examples of various rehabilitation mechanisms with which physiotherapy exercises, in particular gait therapy, can be carried out in an automated manner.

In the course of such kinesitherapy, but also for other medical examination methods and/or therapy methods, it is necessary in daily hospital routine to measure the individual length conditions, the positions of individual joints and the radius of movement of the particular patient in order to adapt the examination and/or therapy equipment used to the particular patient with the aid of the data obtained. Normally, such measurements are taken manually using a measuring tape or, for example, using equipment for measuring the circumference and length of body parts of a recumbent patient, as is known from DE 85 14 240 U1, in which case different persons often carry out these measurements depending on the responsibility for the equipment. Besides the unnecessary repetition, this practice also has the disadvantage that the measurement results often differ on account different persons carrying out the measurements, such that in particular the averages of the measurement values may have considerable errors. Especially if the success of the therapy and therefore the planning of further therapy steps are made dependent on a change of the radius of movement of the patient, the susceptibility of the measurement values to error is of great disadvantage.

In order to overcome this problem, WO 2015/127396 A1 has disclosed a method and an apparatus for measuring the relative orientation and position of adjacent bones to each other. This method and this apparatus are intended in particular for intraoperative determination of different length and orientation parameters of the extremities of a patient in order to permit very precise positioning of orthopedic implants during orthopedic surgery. To this end, the method entails (surgical) fixing of magnetic and/or optical sensors and/or acceleration sensors directly to the hip and femur of the patient. The fixing of the sensors directly to the bone that is to be measured permits a relatively high degree of precision of the measurement parameters. However, on account of its invasive nature, it places an enormous strain on the particular patient and for this reason is suitable only for intraoperative measurements and not, in cases where there is no indication for surgery on the lower extremities of the patient, for obtaining measurement values for physiotherapeutic kinesitherapy.

Moreover, DE 100 60 466 A1 discloses an apparatus for measuring leg movement and for simulation of movement, environment and ground surface, with which apparatus a walking/running movement can be determined in three dimensions and can be "projected" into a virtual environment in the context of a simulation.

SUMMARY OF THE INVENTION

Proceeding from this, the object of the present invention is to make available an improved measuring method and an improved apparatus for determining the length conditions, the position and/or the radius of movement of the lower extremities of a bedridden patient, which determines patient data in a non-invasive manner, which data can be used for further and in particular also automated kinesitherapy, and also for other medical examination methods and/or therapeutic methods.

This object is achieved in the first instance by a measuring method for determining the length conditions, the position and/or the radius of movement of the lower extremities of a bedridden patient, such as hip joint, knee joint and/or upper leg, having the features of the independent method claim, and by an apparatus for carrying out such a measuring method, having the features of the independent apparatus claim. Further advantageous embodiments and developments, which can be used individually or in combination with one another, are the subject matter of the dependent claims.

The measuring method according to the invention is characterized in that at least one knee module of a rehabilitation mechanism is operatively connected to a leg of the patient via an application point; a measuring device is used for recording and/or determining a trajectory solely of the application point during a movement of the leg with the knee module of the rehabilitation mechanism; and a model-generating means is used to create, from the data thus obtained, a kinematic model of the length conditions, the position and/or the radius of movement of at least parts of the lower extremities of the patient.

The application point can also advantageously be the knee joint of the patient.

The determination of the trajectory solely of the application point, in particular of the knee joint, during a movement, in particular during a first movement guided by the therapist or during an automated movement, advantageously permits the creation of a kinematic model of the length conditions, the position and/or the radius of movement of at least parts of the lower extremities of the patient from the determined data. The knee module of the rehabilitation mechanism can then advantageously independently travel along this trajectory and in so doing guide the lower extremities, in particular the leg, of a bedridden patient. Gait therapy adapted to the anatomical conditions of the particular patient is thus possible independently of the availability of treatment personnel.

Moreover, the kinematic model generated in the first movement advantageously supplies anatomical parameters of the patient, for example the length of the upper leg, the position of the hip joint and the actual radius of movement of the patient. Not only can these parameters be used in other therapy forms, for controlling other therapy appliances, in particular automatically driven therapy appliances (robots), they also permit monitoring of the course of treatment and adaptation of the respective therapy movement in the case of measurements carried out at regular time intervals.

Preferably, in one method step, the leg is secured to the knee module via an application point, in particular via the knee joint, the upper leg and/or a lower leg, by means of a knee orthosis. The securing of the leg to the knee module advantageously permits in the first instance, during the process of measuring and/or determining the trajectory of the knee joint, the transmission of force from the leg to the knee module and thus to the measuring device during the first, guided movement of the leg, and then, during the therapy, the transmission of force from the knee module to the leg during the automatic execution of the therapy movement.

It is also preferable according to the invention that, in one method step, the measuring device, proceeding from a starting position, records a manually guided and/or automated movement of the leg, in particular as a trajectory of an application point, in particular of the knee joint, in the form of coordinate pairs or time-dependently in the form of coordinate triplets. A starting position is established manually be the therapist in accordance with the movement possibilities of the particular patient or else in an automated manner on the basis of plausible estimated values of the anatomical conditions of the particular patient. The resulting position of the application point, in particular of the knee joint, can advantageously form the reference point for further movements in the subsequent course of therapy.

In one embodiment, it has proven expedient that the measuring device determines the trajectory of the attachment point, in particular of the knee joint, in the form of coordinate pairs or time-dependently in the form of coordinate triplets, with the aid of at least two sensors from the angle positions of eccentrics that are driven by electric motor. By determination of the coordinate pairs or coordinate triplets of the trajectory of the application point, in particular of the knee joint, from the angle positions of the eccentrics, it is advantageously possible to dispense with other sensors. This can advantageously cut down on the costs for additional sensor technology and on the time taken for sensor-based and/or manual measurement, and can at the same time supply comparatively accurate, reproducible measurement results, which can in turn be used to generate a very precise and reproducible model of the bedridden patient.

According to the invention, it is additionally preferable that, in at least one method step, determined coordinate pairs or coordinate triplets are compared with a model function in the form of a coordinate equation, and in this way, in the context of a curve-fitting, the position of a rotation point, in particular of the hip joint, and/or the length between application point and rotation point, in particular the length of the upper leg of the bedridden patient, and an angle ($\theta\_DP$) between two points on the trajectory ($T_n$; $T_{n+1}$) and the rotation point (DP) are determined from the coordinate pairs or triplets. The curve fitting, in particular based on a least-squares optimization of the measurement data proceeding from a model function or also a so-called spline interpolation, to the respectively determined trajectory of the application point, in particular of the knee joint, advantageously permits the determination of the position for the rotation point, in particular for the hip joint, and also the length between application point (AP) and rotation point (DP), in particular the length of the upper leg, solely from the previously recorded trajectory of the application point, in particular of the knee joint, during the manually guided and/or automated movement. This "initializing" movement is obligatory and would have to be carried out by the therapist in any case to determine the radius of movement that can actually be managed by the patient.

In one embodiment, particularly in (young) patients, with an approximately fixed position of the rotation point, in particular of the hip joint, it has proven expedient if, as model function, use is made in particular of a coordinate equation $(Y_n - Y_H)^2 + (Z_n - Z_H)^2 = L_0^2$ for a circle; as the parameter for the center point of the circle, use is made of the position of the rotation point, in particular of the hip joint; and, as the radius of the circle, use is made of the length between application point and rotation point, in particular the length of the upper leg of the bedridden patient.

Alternatively, in one embodiment, particularly in (older) patients with a "variable" position of the rotation point, in particular of the hip joint, i.e. a rotation point position that changes during a movement, it has also proven expedient if, as model function, use is made in particular of the coordinate equation $$\frac{(Y_n - M_Y(Y_H))^2}{L_0^2} + \frac{(Z_n - M_Z(Z_H))^2}{(L_0 \pm \Delta L)^2} = 1$$

for an ellipse; as the parameter for the center point of the ellipse, use is made of a function according to the position of the rotation point, in particular of the hip joint; and, as the semi-major axis of the ellipse, use is made of the length between application point and rotation point, in particular the length of the upper leg of the bedridden patient.

The use of the coordinate equation of a circle as model function can advantageously offer a mathematically simple possibility of determining the position of the rotation point, in particular of the hip joint, and the length between application point and rotation point, in particular the length of the upper leg of the patient, whereas the use of other more complex model functions, for example the coordinate equation of an ellipse, can advantageously reflect cases in which the position of the rotation point, in particular of the hip joint of the patient, slightly changes (varies) during the movement of the leg.

In a further embodiment of the invention, it has proven expedient if, in one method step, a control module is provided for controlling planned rehabilitation movements at least of the joints, muscles and tendons of the legs of the bedridden patient by means of the knee module, wherein the control module preferably determines, from the patient-specific data generated from the kinematic model, trajectories, in particular new, modified trajectories, for the rehabilitation movements of the leg of a patient with respect to the application point, in particular of the knee joint, and, on the basis of these trajectories, controls the knee module preferably according to user inputs. After the single recording of the manually guided and/or automated trajectory of the application point, in particular of the knee joint, it is then possible, during the actual kinesitherapy, that the previously recorded trajectory is reproduced and/or modified movements according to the new, modified trajectory are performed with the aid of the rehabilitation mechanism and/or knee module. The kinesitherapy of the bedridden patient can in this way be carried out independently of the availability of healthcare personnel and can be provided at any time and as often as required.

Also of advantage is an embodiment in which the rehabilitation mechanism and/or the knee module, during the manually guided and/or automated movement of the leg, is controlled with the aid of the control module in such a way that the effect of forces along an axis, defined by application point and rotation point, through the rehabilitation mechanism and/or the knee module on the leg of the bedridden patient is avoided. In this way, in the first movement guided manually by the therapist and/or in an automated manner, it is advantageously possible to avoid distortion of the measurement values by an influence of the rehabilitation mechanism and/or by the knee module on the natural movement of the patient. In addition, such control can make the operation of the rehabilitation mechanism and/or of the knee module easier, since mechanical resistances of the equipment do not have to be overcome by the therapist.

In addition, an embodiment of the measuring method according to the invention has proven expedient in which the control module, on the basis of calculated trajectories for the application point, in particular for the knee joint, controls the knee module and/or the rehabilitation mechanism in such a way that the application point, in particular the knee joint, of the bedridden patient is moved along these in particular new, modified trajectories with the aid of the knee module and optionally of the knee orthosis. Without new measurements having to be carried out, the movement sequence during the physiotherapy exercises can thus be automatically adapted to the therapy profile, in particular with respect to a changing radius of movement or range of movement of the patient.

In a preferred embodiment according to the invention, it has additionally proven expedient if, in one method step, after each automated movement of the leg, new values are calculated from each new time-dependently recorded trajectory of the application points for the length between application point and rotation point, the position of the rotation point, and the angle between two points on the trajectory and the rotation point, and these new values are compared with the corresponding values of previously measured trajectories.

According to the invention, it is additionally preferable if, in one method step, on the basis of the comparison of the values for the length between application point and rotation point, the position of the rotation point, and the angle between two points on the trajectory and the rotation point, in each case of two successively measured trajectories, an updated model with improved values for the length between application point and rotation point, the position of the rotation point, and an angle between the two points on the trajectory and the rotation point is generated by means of an optimization algorithm, in particular a least-squares algorithm.

Finally, an embodiment has proven expedient in which, in one method step, the values of the updated model serve as a basis for a further automated movement of the leg.

If, after each automated movement of the leg, new values are calculated from each new time-dependently recorded trajectory of the application point for the length between application point and rotation point, the position of the rotation point, and the angle between two points on the trajectory and the rotation point, and these new values are compared with the measured values of previous cycles and optimized, taking into consideration the trajectories of previous cycles, i.e. previous automated movements of the leg of a patient, and the values thus optimized for the length between application point and rotation point, the position of the rotation point, and the angle between two points on the trajectory and the rotation point are used as a basis for a further automated movement of the leg, the therapy movement guided in an automated manner by the rehabilitation mechanism can advantageously be adapted to the anatomical conditions of the particular patient during the therapy. In this way, the rehabilitation mechanism also has the possibility of reacting in a likewise automated manner to deviations, for example on account of the knee orthosis slipping and/or the whole body of the patient moving with respect to the rehabilitation mechanism, or to other changes, near-instantaneously, in particular after each cycle, i.e. after an automated and complete therapeutic movement of the leg of a patient, and, if appropriate on the basis of error limit values, of carrying out corrections to the automated therapeutic movement.

This possibility of "machine learning" advantageously makes it possible to offer the patient, with the aid of a rehabilitation mechanism, an individualized form of kinesitherapy which, by virtue of the error correction possibility provided, is robust against external interference whether caused by changes to the equipment itself or by changes of the patient during use.

Compared to apparatuses of the type in question, an apparatus according to the invention for carrying out such a measuring method is characterized by a measuring device for recording and/or determining a trajectory solely of the application point, in particular of the knee joint, during the movement of the leg; and by a model-generating means for creating a kinematic model of the length conditions, the position and/or the radius of movement of at least parts of the lower extremities of the patient from the data thus obtained.

The apparatus according to the invention advantageously permits the automatic recording and/or determination of a trajectory of the application point, in particular of the knee joint, during the movement of the leg of a bedridden patient solely from kinematic motion data and without the use of other sensors, for example optical sensors. The apparatus according to the invention also advantageously makes it possible to create, from the data thus obtained, a kinematic model of the length conditions, the position and/or the radius of movement of at least parts of the lower extremities of the patient.

In a preferred embodiment of the apparatus, the measuring device comprises at least two sensors for determining the angle position of the shaft of the electric motor and/or of the eccentrics. In this way, it is advantageous that no further sensor technology is required, since the rotary encoders of servo motors can be used as sensors.

It is also advantageous if a control module for controlling planned rehabilitation movements at least of the joints, muscles and tendons of the legs of the bedridden patient by means of the knee module is provided, wherein the control module is preferably configured to determine, from the patient-specific data generated from the kinematic model, trajectories, in particular new, modified trajectories, for the rehabilitation movements of the leg of a patient with respect to the application point, in particular the knee joint, and, on the basis of these trajectories, to control the knee module preferably according to user inputs. With the aid of the control module, the rehabilitation mechanism and/or the knee module can advantageously be controlled in such a way that the rehabilitation movement follows a previously defined trajectory.

In a further preferred embodiment of the apparatus, the knee module comprises at least one knee orthosis receiving the knee joint of the bedridden patient; a connection element connected to the knee orthosis; an extension arm on which the connection element is secured; and a mechanical device which can be driven by means of a control module and which introduces a defined force into the knee orthosis, via the extension arm and the connection element, in such a way that the joints, muscles and tendons of the leg perform planned rehabilitation movements via the application point, in particular via the therein received knee joint of the bedridden patient. A configuration of this kind can advantageously permit the movement of the knee orthosis with respect to the knee module and thus advantageously increase the degrees of freedom of movement of the therapy movement.

Finally, according to one embodiment, it is advantageous if the rehabilitation mechanism comprises at least one angle sensor which monitors the angle adopted by a connection element to the knee orthosis and/or to an extension arm; and/or a force sensor which monitors the force introduced into the knee orthosis via the extension arm and the connection element. In the case of a knee orthosis that is movable with respect to the knee module, which can advantageously increase the number of degrees of freedom of movement for the therapy movement, the angle sensor permits, in combination with the sensors, the automatic recording and/or determination of the trajectory of the knee joint.

The present invention advantageously permits the determination of the length conditions, the position and/or the radius of movement of the lower extremities of a bedridden patient, such as hip joint, knee joint and/or upper leg, without surgical intervention, solely on the basis of the recording and/or determination of the trajectory of an application point, in particular the knee joint, during at least one initializing movement of the patient. The invention does away with the need for complex and expensive sensor technology and advantageously makes available a kinematic model of the radius of movement of the patient, the parameters of which kinematic model can serve as a basis for establishing new therapeutic procedures within kinesitherapy and also as a starting model for other automated therapeutic methods and examination methods. By way of a "machine learning" functionality, the present invention also makes it possible to offer the patient, with the aid of a rehabilitation mechanism, an individualized kinesitherapy which, by virtue of the error correction possibility provided, is robust against external interference.

BRIEF DESCRIPTION OF THE SEVERAL VIEWS OF THE DRAWING

Additional details and further advantages of the invention are described below on the basis of preferred illustrative embodiments, to which the invention is not limited however, and in conjunction with the attached schematic drawing, in which.

DESCRIPTION OF THE INVENTION

In the following description of preferred embodiments of the present invention, identical reference signs designate identical or comparable components.

Figure 1:
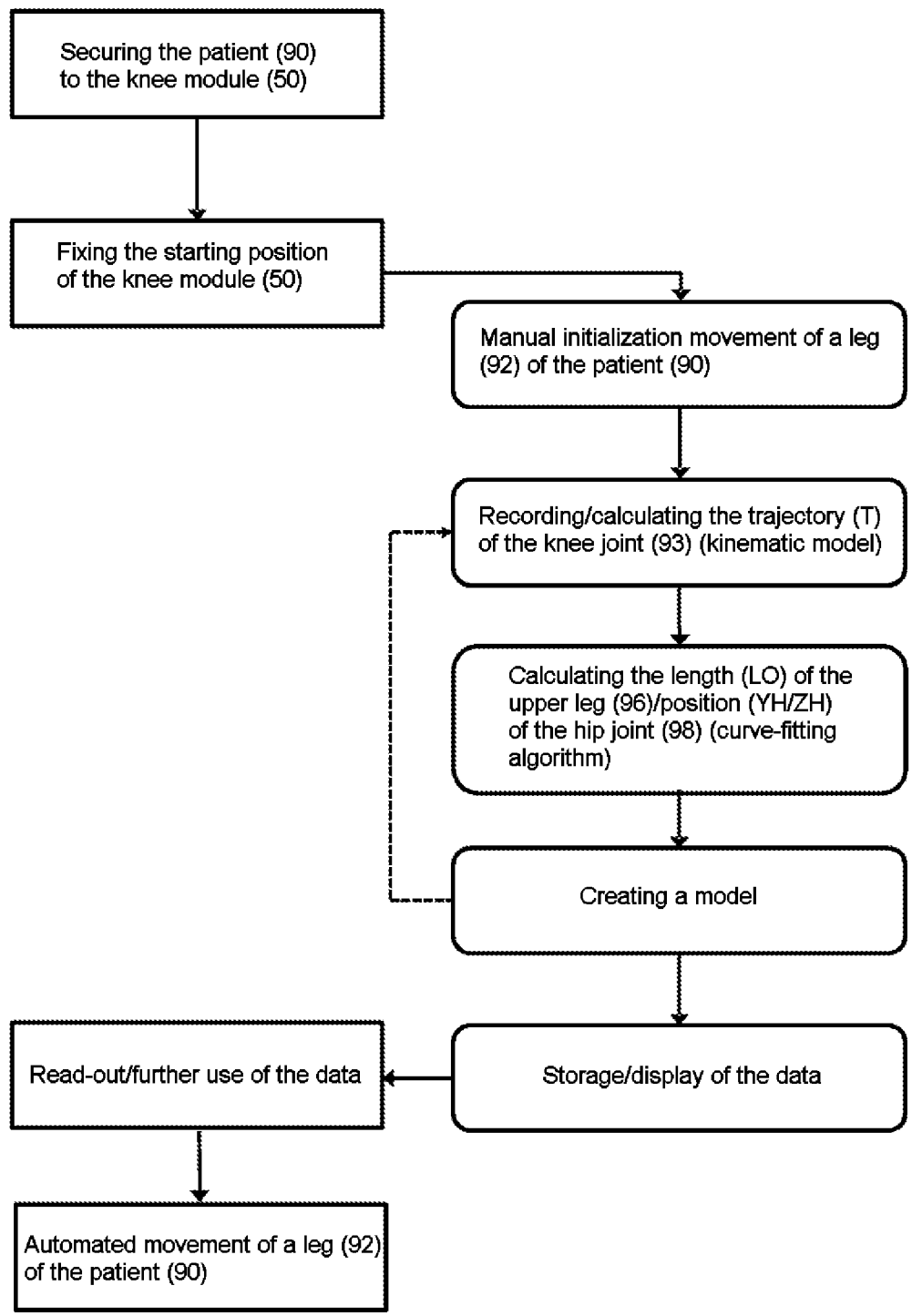
FIG. 1 shows a first flowchart of a measuring method for determining the length conditions, the position and/or the radius of movement of the lower extremities of a bedridden patient, such as hip joint, knee joint and/or upper leg.

FIG. 1 shows a flowchart of a measuring method for determining the length conditions, the position and/or the radius of movement of the lower extremities of a bedridden patient 90, such as hip joint 98, knee joint 93 and/or upper leg 96.

First, at least one knee module 50 of a rehabilitation mechanism 30 is operatively connected to a knee joint 93 of the patient 90. For this purpose, the leg 92, in particular the knee joint 93, the upper leg 96 and/or a lower leg 97, can be secured to the knee module 50 by means of a knee orthosis 51 for example (cf. also FIG. 4 and FIG. 6).

In a second method step, by means of a measuring device 68, a trajectory T of the knee joint 93 can then be recorded and/or determined during a movement of the leg 92, in particular during an initialization movement performed by a therapist, with the knee module 50 of the rehabilitation mechanism 30. During this initialization movement, it may be advantageous if the rehabilitation mechanism 30 and/or the knee module 50 are controlled with the aid of the control module 60, during the manually guided movement of the leg 92, in such a way that the effect of forces N exerted on the leg 92 of the bedridden patient 90 by the rehabilitation mechanism 30 and/or the knee module 50 is avoided.

Figure 10B:
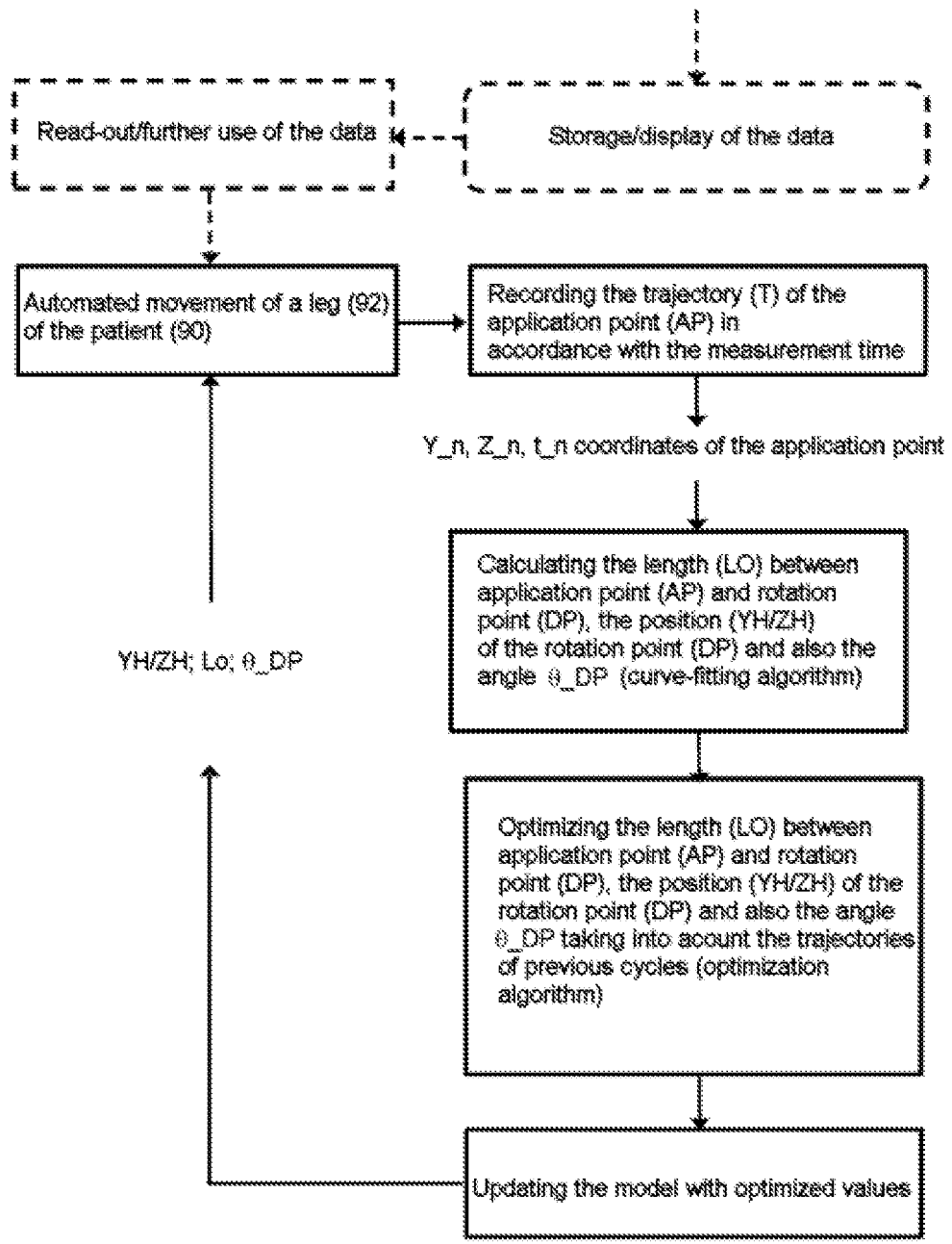
FIGS. 10a and b show a second flowchart (divided between the two figures) of a preferred measuring method according to the invention for determining the length conditions, the position and/or the radius of movement of the lower extremities of a bedridden patient, such as hip joint, knee joint and/or upper leg, with the possibility of automatic error correction and rapid adaptation to external interference.

FIGS. 10a and 10b show a second flowchart (divided between the two figures) of a preferred measuring method according to the invention for determining the length conditions, the position and/or the radius of movement of the lower extremities of a bedridden patient 90, such as hip joint 98, knee joint 93 and/or upper leg 96 with the possibility of automatic error correction and rapid adaptation to external interference. The initialization of a model is effected in a way comparable to that shown in the first flowchart of FIG. 1, wherein the measuring device 68, this time proceeding from a starting position $P_0$, records a manually guided and/or automated movement of the leg 92, in particular as trajectory $T_n$; $T_{n+1}$ of a an application point AP in the form of coordinate triplets $Y_1/Z_1/t_1$, $Y_2/Z_2/t_2$, ..., $Y_n/Z_n/t_n$, in a time-dependent manner. As the application point AP via which at least one knee module 50 of a rehabilitation mechanism 30 is operatively connected to a leg 92 of the patient 90, it is possible to choose preferably the knee joint 93, the upper leg 96 or lower leg 97, or indeed any point of the leg 92.

The measuring device 68 can determine the trajectory $T_n$; $T_{n+1}$ of the application point AP, in particular of the knee joint 93, in turn in the form of coordinate triplets $Y_1/Z_1/t_1$, $Y_2/Z_2/t_2$, ..., $Y_n/Z_n/t_n$ with the aid of at least two sensors 681; 682 from the angle positions of eccentrics 63; 64 that are driven by an electric motor.

The time-dependent recording of the trajectory $T_n$; $T_{n+1}$ of an application point AP in the form of coordinate triplets $Y_1/Z_1/t_1$, $Y_2/Z_2/t_2$, ..., $Y_n/Z_n/t_n$ affords in the first place the advantage that, by assigning a measurement time $t_1$, $t_2$, ..., $t_n$ to the measured coordinate pairs $Y_1/Z_1$, ..., $Y_n/Z_n$, it is advantageously possible to distinguish between a lifting movement and lowering movement of the leg 92. In the second place, the sequence of the measurement values that can be determined in this way can advantageously be taken into account during the optimization by means of an optimization algorithm and can thus improve the optimization results. This is based on the understanding that measurement values lying close to each other in time ought also to be adjacent on a measured trajectory $T_n$; $T_{n+1}$ and therefore ought also to have similar physical properties.

Following the initialization, it is now possible that, after each automated movement of the leg 92, new values for the length $L_0$ between application point AP and rotation point DP, the position $Y_H(t)/Z_H(t)$ of the rotation point DP and the angle θ_DP between two points on the trajectory $T_{n+1}$ and the rotation point DP can be calculated from each new, time-dependently recorded trajectory $T_{n+1}$ and compared with the corresponding values of previously measured trajectories $T_n$. The position $Y_H(t)/Z_H(t)$ of the rotation point DP, wherein the rotation point DP can be for example the hip joint 98 of the patient 90, can be an approximately fixed position $Y_H(t)/Z_H(t)$ with $Y_H(t_1)=Y_H(t_2)=...=Y_H(t_n)$ and $Z_H(t_1)=Z_H(t_2)=...=Z_H(tn)$ in space, i.e. a real rotation "point", or, as can often be the case particularly in older patients 90 on account of wear of the acetabulum, it can be a "variable" time-dependent position $Y_H(t)/Z_H(t)$ of the rotation point DP, in particular of the hip joint 98 of the patient 90, which position changes during a movement.

Based on the comparison of the values for the length Lo between application point AP and rotation point DP, the position YH(t)/ZH(t) of the rotation point DP and the angle between two points on the trajectory $T_n$; $T_{n+1}$ and the rotation point DP of in each case two successively measured trajectories $T_n$, $T_{n+1}$, it is then possible, by means of an optimization algorithm, in particular a least-squares algorithm, to generate an updated model with improved values for the length $L_O$ between application point AP and rotation point D, the position YH(t)/ZH(t) of the rotation point DP and an angle θ_DP between two points on the trajectory $T_n$; $T_{n+1}$ and the rotation point DP, the values of which updated model can advantageously serve as a basis for a further automated movement of the leg 92.

The measuring method according to the invention thus means that an apparatus 1 according to the invention for carrying out such a measuring method can advantageously undergo "machine learning" of a therapy movement during the automated movement sequence ("cycle"). This possibility of "machine learning" advantageously makes it possible to offer the patient 90, with the aid of a rehabilitation mechanism 30, an individualized form of kinesitherapy which, by virtue of the error correction possibility provided, is robust against external interference whether caused by changes to the rehabilitation mechanism 30 itself or by changes of the patient 90 during use.

Figure 2A:
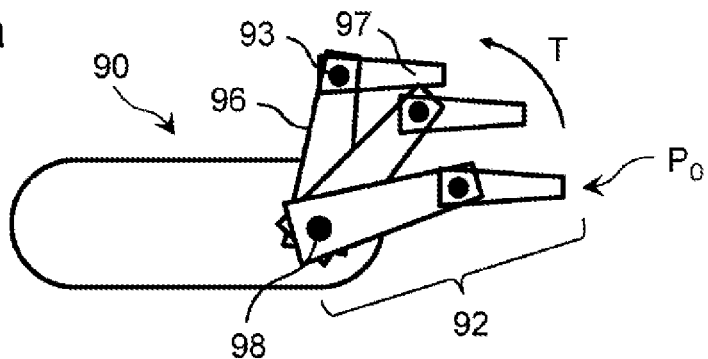
FIG. 2a shows a torso and a leg of a bedridden patient in a possible movement of the leg during kinesitherapy.
Figure 2B:
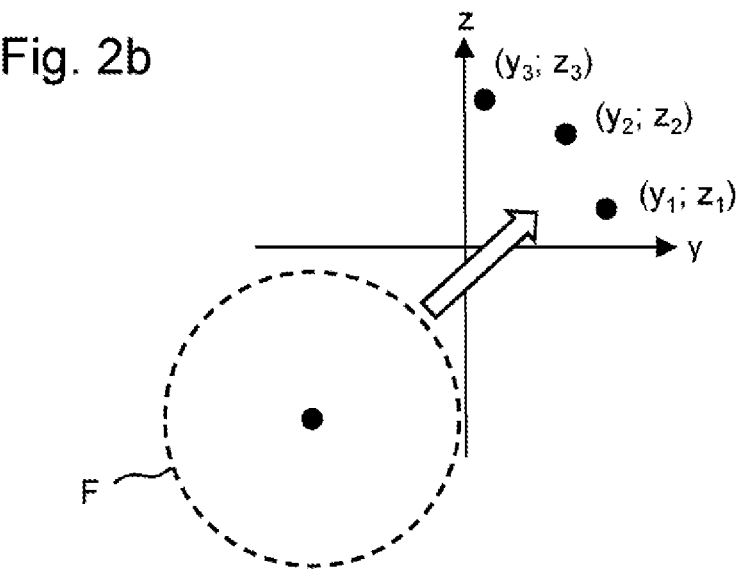
FIG. 2b shows a knee joint trajectory resulting from the movement in FIG. 2a, on the basis of three coordinate pairs within a basic coordinate system, and a possible model function prior to curve fitting.
Figure 2C:
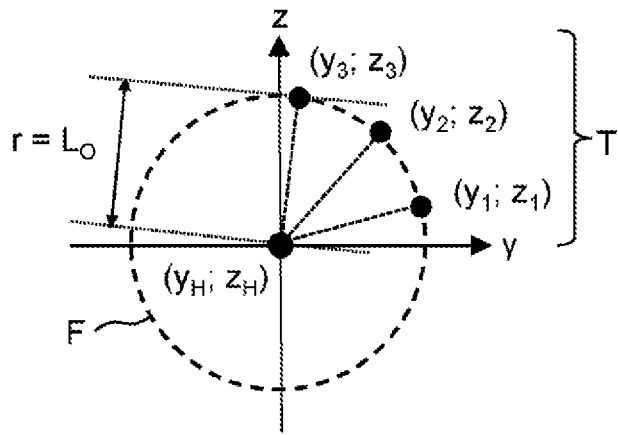
FIG. 2c shows the trajectory of the knee joint from FIG. 2b with an adapted model function, here in the form of a circle, and also the parameters, generated from the adaptation, for the length of an upper leg and for the position of the hip joint.

FIGS. 2a to 2c illustrate this recording and/or determination process.

FIG. 2a shows a torso and a leg 92 of a bedridden patient 90 in a possible movement of the leg 92 during kinesitherapy.

FIG. 2b shows, resulting from this movement, a trajectory T of the knee joint 93 on the basis of three coordinate pairs $Y_n/Z_n$ within a basic coordinate system, and also a possible model function F prior to curve fitting. Proceeding from a starting position $P_0$, and during a manually guided movement of the leg 92, the trajectory T of the knee joint 93 can be recorded, preferably by a measuring device 68, in particular in the form of coordinate pairs $Y_1/Z_1$, $Y_2/Z_2$, ..., $Y_n/Z_n$. The determination of the coordinate pairs $Y_1/Z_1$, $Y_2/Z_2$, ..., $Y_n/Z_n$ can advantageously be effected with the aid of at least two sensors 681; 682 from the angle positions of eccentrics 63; 64 that are driven by electric motor (cf. FIGS. 4, 5, 7a to c).

The trajectory T is advantageously determined by comparing the identified coordinate pairs $Y_1/Z_1$; $Y_2/Z_2$; .../...; $Y_n/Z_n$ with a model function in the form of a coordinate equation.

As model function F, it is possible for example to use a coordinate equation $(Y_n-Y_H)^2+(Z_n-Z_H)^2=L_O^2$ for a circle with the position $Y_H/Z_H$ of the hip joint 98 as the center point of the circle and with the length $L_O$ of the upper leg 96 of the bedridden patient 90 as the radius of the circle.

FIG. 2c shows the trajectory T of the knee joint 93 from FIG. 2b with an adapted model function F in the form of the coordinate equation of a circle, and also the parameters, generated from the adaptation, for the length $L_O$ of an upper leg 96 and for the position $Y_H/Z_H$ of the hip joint 98.

As an alternative to this, it is also possible to use as model function F the coordinate equation $$\frac{(Y_n - M_Y(Y_H))^2}{L_0^2} + \frac{(Z_n - M_Z(Z_H))^2}{(L_0 \pm \Delta L)^2} = 1$$

for an ellipse, wherein the parameter for the center point of the ellipse can now be a function $M_Y(Y_H)/M_Z(Z_H)$ in accordance with the position $Y_H/Z_H$ of the hip joint 98, and the parameter for the semi-major axis of the ellipse can be the length $L_O$ of the upper leg 96 of the bedridden patient 90. The term $L_0 \pm \Delta L$ describes a possible shift of the position $Y_H/Z_H$ of the hip joint 98 during the movement.

Figure 3:
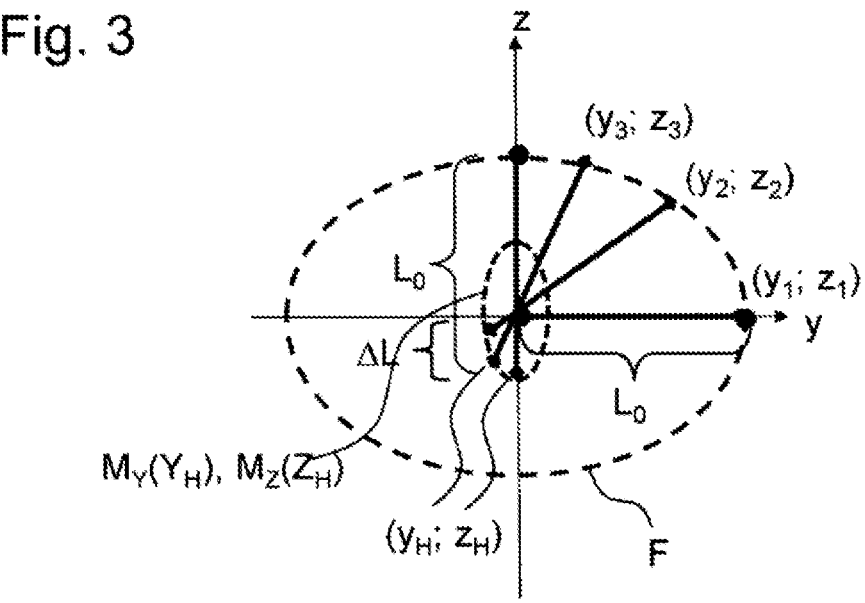
FIG. 3 shows the adaptation of the model function of an ellipse to the coordinate pairs of a trajectory of the knee joint.

FIG. 3 shows an example of such an adaptation of the model function F of an ellipse to the coordinate pairs $Y_n/Z_n$ of a trajectory T of the knee joint 93, wherein the function $M_Y(Y_H)/M_Z(Z_H)$ resulting from the shift of the position $Y_H/Z_H$ of the hip joint 98 can likewise be represented, as can be seen, as an elliptical function, but with a semi-major axis perpendicular to the semi-major axis of the model ellipse.

Finally, from the data thus obtained, it is possible, with the aid of a model-generating means 69, to create a kinematic model of the length conditions, the position and/or the radius of movement of at least parts of the lower extremities of the patient 90.

With the aid of a control module 60 for controlling planned rehabilitation movements of at least the joints, muscles and tendons of the legs 92 of the bedridden patient 90 by means of the knee module 50, it is then possible, in a further method step, preferably using the patient-specific data generated from the kinematic model, to determine trajectories T, in particular new, modified trajectories T, for the rehabilitation movements of the knee joint 93 and, on the basis of these trajectories T, to control the knee module 50 preferably in accordance with user inputs. On the basis of the calculated trajectories T for the knee joint 93, the control module 60 can control the knee module 50 and/or the rehabilitation mechanism 30 in such a way that the knee joint 93 of the bedridden patient 90 is moved, with the aid of the knee module 50 and optionally the knee orthosis 51, along these in particular new and modified trajectories T.

Figure 8:
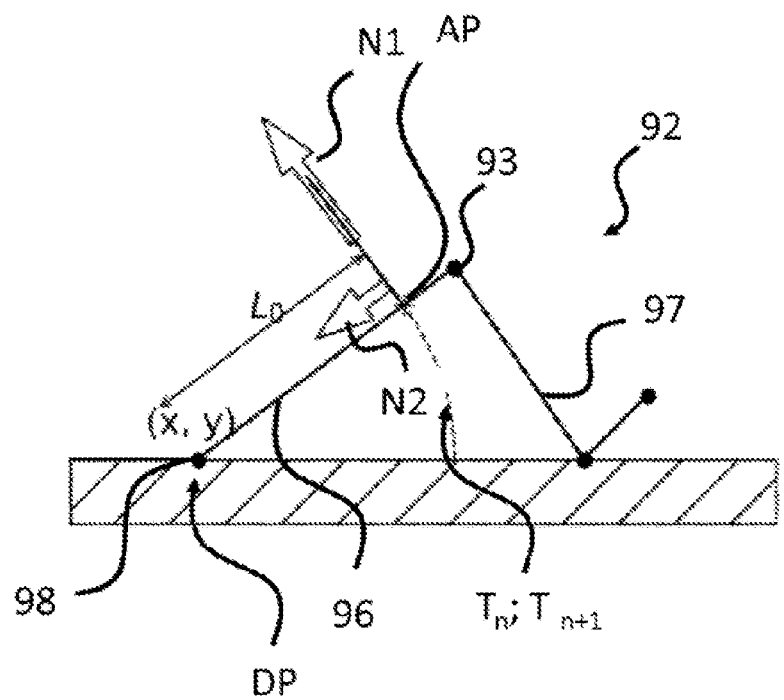
FIG. 8 shows a trajectory of an application point on an upper leg of a patient with an adapted model function and the force exerted on the leg of the patient via the application point when the leg is elevated by a rehabilitation mechanism and/or a knee module, and also the effect of forces on the leg of the bedridden patient along an axis defined by application point and rotation point.

FIG. 8 correspondingly shows a trajectory $T_n$; $T_{n+1}$ of an application point AP on an upper leg 96 of a patient 90 with an adapted model function F, and the force N1 exerted on the leg 92 of the patient 90 via the application point AP during elevation of the leg 92 by a rehabilitation mechanism 30 and/or a knee module 50, and also the effect of forces N2 on the leg 92 of the bedridden patient 90 along the axis application point AP-rotation point DP.

Figure 9:
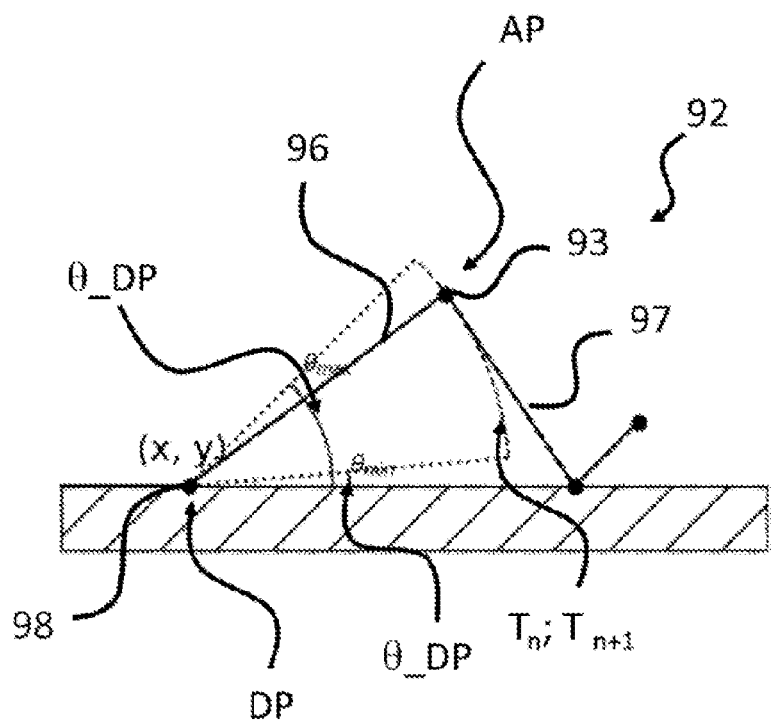
FIG. 9 shows angles determined, in the context of curve fitting, between two points on the trajectory and the rotation point, here specifically an angle $\theta_{max}$ with maximum elevation of the application point and an angle $\theta_{min}$ with minimal elevation of the application point.

FIG. 9 shows by way of example two angles θ_DP, determined in the context of a curve fitting, between in each case two points on the trajectory $T_n$; $T_{n+1}$ and the rotation point DP, here specifically an angle $\theta_{max}$ with maximum elevation of the application point AP and an angle $\theta_{min}$ with minimum elevation of the application point AP.

The difference of the angles $\theta_{min}$ and $\theta_{max}$ advantageously provides information on the mobility of the patient 90 and therefore on the progress made by the therapy.

FIGS. 4 to 7c show, by way of example, various views of an embodiment of an apparatus for carrying out the measuring method according to the invention. As regards the mechanical functioning of the rehabilitation mechanism 30 and of the knee module 50 as such, reference is made to the entirety of WO 2017/063639 A1 from the applicant.

Figure 4:
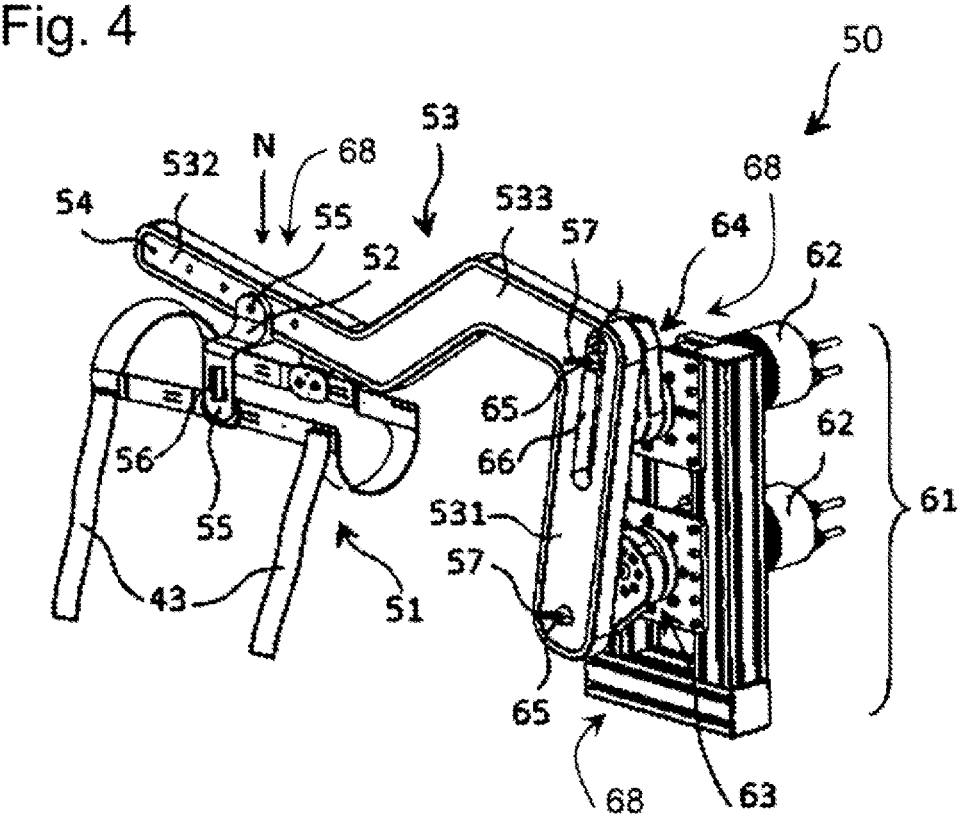
FIG. 4 shows a perspective view of a left-hand extension arm of a knee module of a rehabilitation mechanism of an apparatus for carrying out the method according to the invention.
Figure 5:
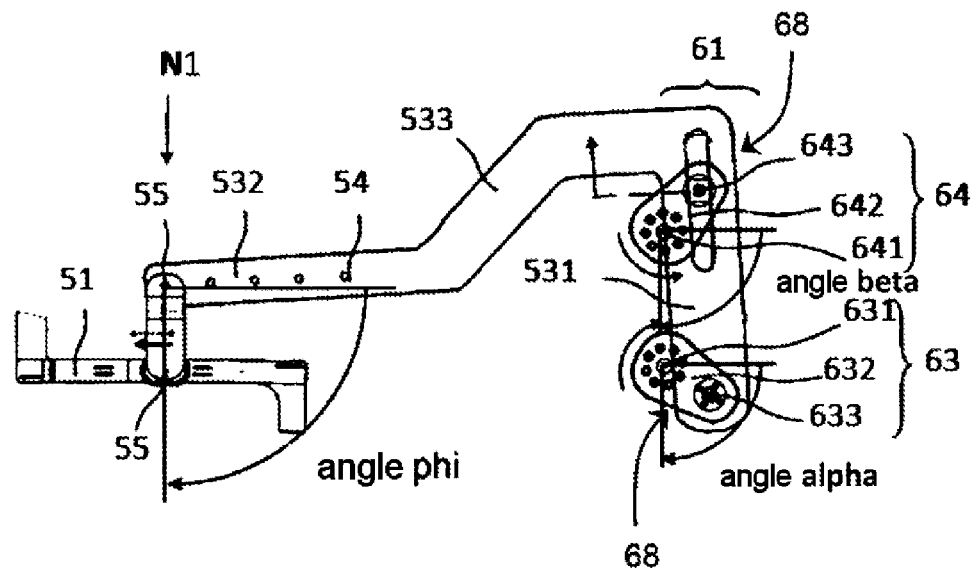
FIG. 5 shows an example of the extension arm from FIG. 4 in an enlarged side view.

FIGS. 4 and 5 (corresponding to FIGS. 3 and 12 of WO 2017/063639 A1) show, by way of example, a left extension arm 53 of a knee module 50 of a rehabilitation mechanism 30 of an apparatus for carrying out the measuring method according to the invention, in a perspective view (FIG. 4) and in an enlarged side view (FIG. 5).

Figure 6:
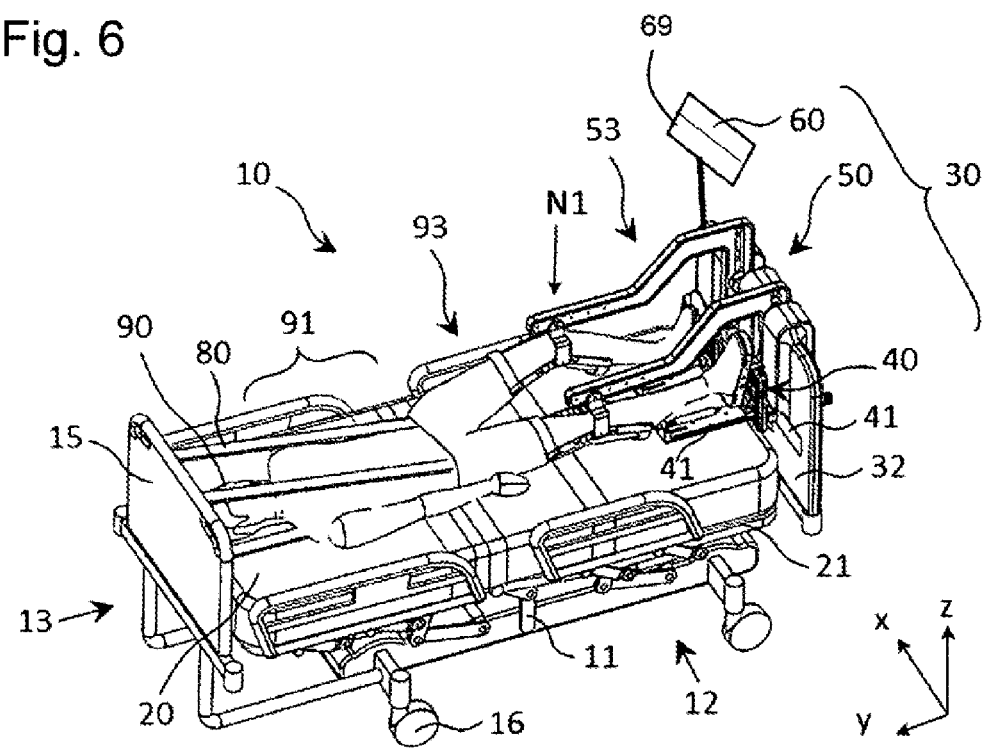
FIG. 6 shows a perspective view of a bedridden patient secured in a conventional bed according to the prior art, in particular an intensive care bed, with the applied knee module and foot module of a rehabilitation mechanism, before the bed is moved to a vertical position.
Figure 7:
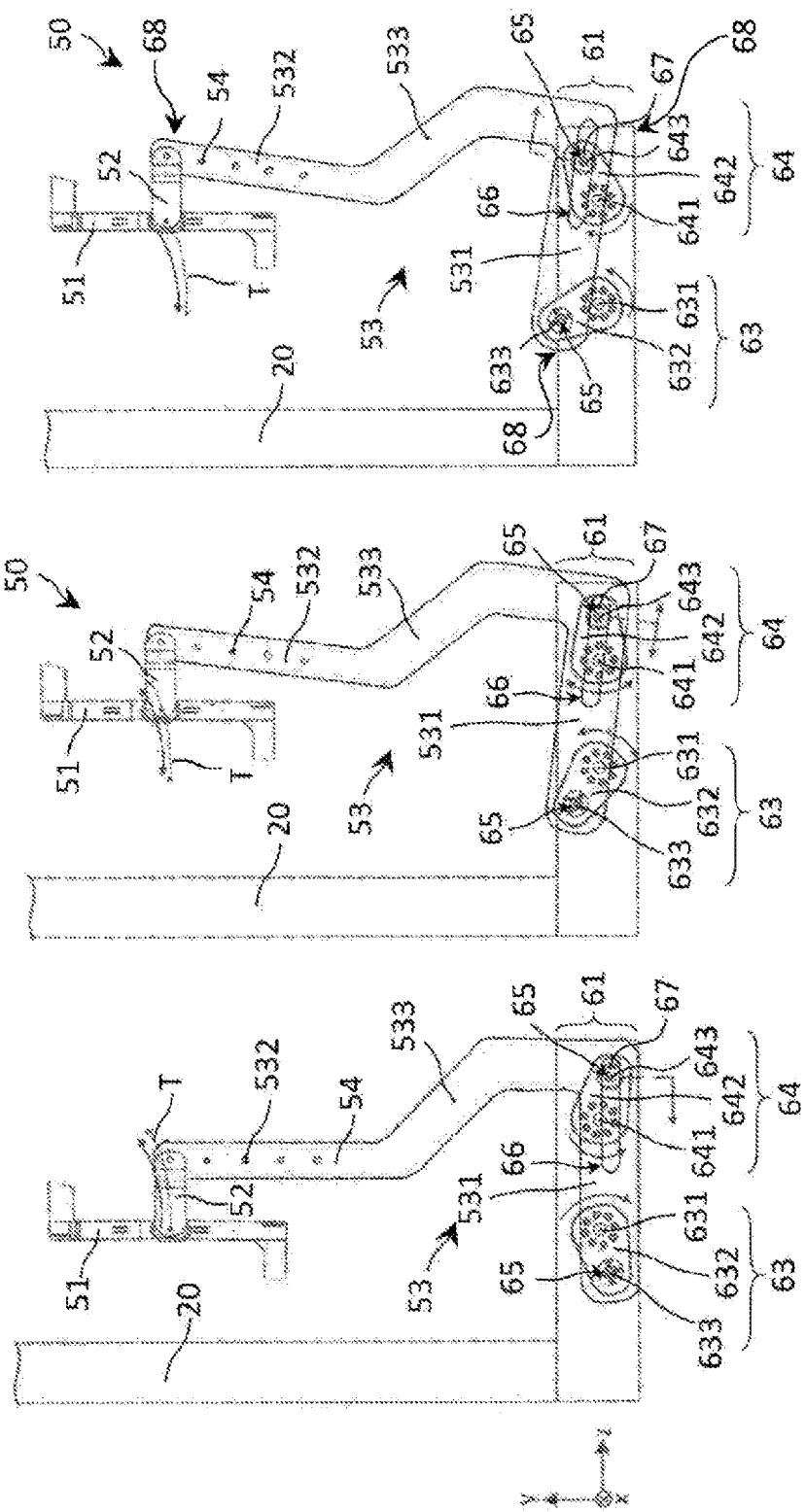
FIGS. 7a to c show a trajectory, generated by the rehabilitation mechanism via the knee orthosis, for flexion or extension of the leg of a patient.

FIG. 6 (corresponding to FIG. 4 of WO 2017/063639 A1) shows a perspective side view of a bedridden patient 90 secured in a conventional bed according to the prior art, in particular an intensive care bed, with the fitted knee module 50 and foot module 40 of a rehabilitation mechanism 30 prior to the bed being moved to a vertical position.

The apparatus according to the invention for carrying out the measuring method comprises at least one rehabilitation mechanism 30 with at least one knee module 50 which can be operatively connected to the knee joint 93 of a patient 90 and comprises at least one electric motor 62 or, as shown in FIG. 4, at least two electric motors 62 for driving at least two eccentrics 63; 64.

The apparatus according to the invention additionally comprises a measuring device 68 for recording and/or determining a trajectory T of the knee joint 93 during the movement of the leg 92, wherein the measuring device 68 can preferably comprise at least two sensors 681; 682 for determining the angle position of the shaft of the one or more electric motors 62 and/or of the eccentrics 63; 63.

In addition, the apparatus 1 according to the invention comprises a model-generating means 69 for creating a kinematic model of the length conditions, the position and/or the radius of movement of at least parts of the lower extremities of the patient 90 from the data obtained by the measuring device 68 recording and/or determining a trajectory T of the knee joint 93 during the movement of the leg 92.

FIG. 6 additionally shows a control module 60 for controlling planned rehabilitation movements of at least the joints, muscles and tendons of the legs 92 of the bedridden patient 90 by means of the knee module 50, which control module 60 can preferably be configured to determine, from the patient-specific data generated from the kinematic model, trajectories T, in particular new, modified trajectories T, for the rehabilitation movements of the knee joint 93 and, on the basis of these trajectories T, to control the knee module 50 preferably in accordance with user inputs.

The knee module 50 preferably comprises at least one knee orthosis 51 receiving the knee joint 93 of the bedridden patient 90, a connection element 52 connected to the knee orthosis 51, an extension arm 53 on which the connection element 52 is secured, and a mechanical device 61 which can be controlled by means of a control module 60 and which introduces a defined force N into the knee orthosis 51, via the extension arm 53 and the connection element 52, in such a way that the joints, muscles and tendons of the leg 92 perform planned rehabilitation movements via the knee joint 93 of the bedridden patient 90.

FIGS. 7a to 7c illustrate a trajectory T, generated by the rehabilitation mechanism 30 via the knee orthosis 51, for flexion and extension of the leg 92 of a patient 90. By way of the connection element 52, the knee orthosis 51 can be either rigidly connected to the extension arm 53, or, as can be seen here, it can be articulated movably on the extension arm 53. In the latter case, i.e. in the case of the movable articulation and the associated greater number of degrees of freedom, a further measuring device 68, in particular in the form of an angle sensor 55, can preferably be provided for exact recording and/or determination of the trajectory T of the knee joint 93.

Finally, FIG. 5 shows an example of a rehabilitation mechanism 30 with an angle sensor 55 which monitors the angle adopted by a connection element 52 to the knee orthosis 51 and/or to the extension arm 53. Alternatively or in addition to this, a force sensor 56 can also be provided which monitors the force N introduced into the knee orthosis 51 via the extension arm 53 and the connection element 52.

The present invention relates to a measuring method for determining the length conditions, the position and/or the radius of movement of the lower extremities of a bedridden patient 90, and an apparatus 1 for carrying out such a method, in which at least one knee module 50 of a rehabilitation mechanism 30 is operatively connected to a knee joint 93 of the patient 90, a measuring device 68 is used to record and/or determine trajectory T of the knee joint 93 during a movement of the leg 92 with the knee module 50 of the rehabilitation mechanism 30, and, from the data thus obtained, a kinematic model is created by a model-generating means 69. This advantageously permits the determination of the length conditions, the position and/or the radius of movement without surgical intervention during at least one initializing movement. Without the need for expensive sensor technology, the invention advantageously makes available a kinematic model of the radius of movement of the patient 90, the parameters of which model can serve as a basis for establishing new therapeutic procedures within the kinesitherapy, and also as a starting model for automated therapeutic methods and examination methods.

LIST OF REFERENCE SIGNS 10 bed, in particular a care bed, sickbed, hospital bed or intensive care bed
11 bed frame
12 longitudinal sides
13 transverse sides
14 longitudinal barrier
15 transverse barrier
16 castors
20 mattress
21 mattress frame
30 rehabilitation mechanism
32 support plate, for rehabilitation mechanism 30, fastenable to the bed frame 11 or mattress frame 21
40 foot module
41 securing means
42 tread surface
43 fixing straps
50 knee module
51 knee orthosis
52 connection element
53 extension arm
531 distal portion of the extension arm 53
532 proximal portion of the extension arm 53
533 middle portion of the extension arm 53
54 receiving points
55 angle sensor
56 force sensor
57 butterfly nut
60 control module
61 mechanical device
62 electric motor
63 first eccentric
631 eccentric shaft of the first eccentric 63
632 eccentric disk of the first eccentric 63
633 control pin of the first eccentric 63
64 second eccentric
641 eccentric shaft of the second eccentric 64
642 eccentric disk of the second eccentric 64
643 control pin of the second eccentric 64
65 radial bearing
66 sliding bearing
67 slide block
68 measuring device
681 sensor of the first eccentric 63
682 sensor of the second eccentric 64
69 model-generating means
70 adjustment mechanism
80 stabilizing mechanism
90 patient
91 chest—heart/lungs
92 leg
93 knee joint
94 foot
95 sole
96 upper leg
97 lower leg
98 hip joint
F model function
N1 force exerted on the leg 92 of the patient 90 via the application point AP
N2 force along the axis: application point AP-rotation point DP
$T_n$; $T_{n+1}$ trajectories
$L_O$ length of the upper leg 96
$Y_n$ Y coordinates of the trajectory T of the knee joint 93
$Z_n$ Z coordinates of the trajectory T of the knee joint 93
$t_1, t_2, \ldots, t_n$ measurement time
$Y_H/Z_H$ position of the hip joint 98 of the bedridden patient 90
AP application point
DP rotation point
θ_DP angle between two points on the trajectory ($T_n$; $T_{n+1}$) and the rotation point (DP)

The invention claimed is:

1. A measuring method for determining length conditions, position and/or a radius of movement of lower extremities of a bedridden patient, which comprises the steps of:
   operatively connecting at least one knee module of a rehabilitation mechanism to an application point of a leg of the patient;
   using a measuring device for recording and/or determining a trajectory solely of the application point during a movement of the leg with the at least one knee module of the rehabilitation mechanism;
   creating, via a model-generating means, from data thus obtained, a kinematic model of the length conditions, the position and/or the radius of movement of at least parts of the lower extremities of the patient;
   comparing coordinate pairs or coordinate triplets with a model function in a form of a coordinate equation, and in a context of a curve-fitting, a position of a rotation point and/or a length between the application point and the rotation point, and an angle between two points on the trajectory and the rotation point being determined;

using the coordinate equation $$\frac{(Y_n - M_Y(Y_H))^2}{L_0^2} + \frac{(Z_n - M_Z(Z_H))^2}{(L_0 \pm \Delta L)^2} = 1$$

for an ellipse as the model function, where $L_0 \pm \Delta L$ represents a possible displacement of the position of the rotation point during the movement;
  using as a parameter for a center point of the ellipse, a function according to the position of the rotation point; and
  using as a semi-major axis of the ellipse, the length between the application point and the rotation point.

2. The measuring method according to claim 1, wherein the application point is a knee joint of the patient.

3. The measuring method according to claim 1, which further comprises securing the application point of the leg to the knee module by means of a knee orthosis.

4. The measuring method according to claim 1, wherein the measuring device, proceeding from a starting position, records a manually guided and/or automated movement of the leg in a form of coordinate pairs or time-dependently in a form of coordinate triplets.

5. The measuring method according to claim 1, wherein the measuring device determines the trajectory of the application point in a form of the coordinate pairs or time-dependently in a form of the coordinate triplets, with an aid of at least two sensors from angle positions of eccentrics that are driven by an electric motor.

6. The measuring method according to claim 1, wherein the rotation point is a hip joint of the patient.

7. The measuring method according to claim 1, which further comprises:
  providing a control module for controlling planned rehabilitation movements of at least joints, muscles and tendons of legs of the bedridden patient by means of the at least one knee module, wherein the control module:
  determines, from patient-specific data generated from the kinematic model, trajectories for rehabilitation movements of the leg of the patient with respect to the application point; and
  on a basis of the trajectories, controls the at least one knee module.

8. The measuring method according to claim 1, which further comprises controlling the rehabilitation mechanism and/or the at least one knee module, during a manually guided and/or automated movement of the leg, with an aid of a control module in such a way that an effect of forces along an axis, defined by the application point and a rotation point, through the rehabilitation mechanism and/or the at least one knee module on the leg of the bedridden patient is avoided.

9. The measuring method according to claim 7, wherein the control module, on a basis of the trajectories calculated for the application point, controls the at least one knee module and/or the rehabilitation mechanism in such a way that the application point is moved along new, modified trajectories with an aid of the at least one knee module.

10. The measuring method according to claim 7, which further comprises:
  after each automated movement of the leg, calculating new values, from each new time-dependently recorded trajectory of application points, for the length between the application point and the rotation point, the position of the rotation point, and the angle between the two points on the trajectory and the rotation point; and
  comparing the new values with corresponding values of previously measured trajectories.

11. The measuring method according to claim 7, wherein on a basis of a comparison of values for:
  the length between the application point and the rotation point;
  the position of the rotation point; and
  the angle between the two points on the trajectory and the rotation point;
  in each case of two successively measured trajectories, an updated model with improved values for the length between the application point and the rotation point, the position of the rotation point, and the angle between the two points on the trajectory and the rotation point is generated by means of an optimization algorithm.

12. The measuring method according to claim 7, wherein values of an updated model serve as a basis for a further automated movement of the leg.

13. The measuring method according to claim 1, wherein the application point is a hip joint, a knee joint, a lower leg and/or an upper leg of the patient.

14. An apparatus for carrying out a measuring method for determining length conditions, a position and/or a radius of movement of lower extremities of a bedridden patient, the apparatus comprising:
  a rehabilitation mechanism having at least one knee module operatively connected to an application point of a leg of the patient and with at least two eccentrics and at least one electric motor for driving said at least two eccentrics on said at least one knee module;
  a measuring device for recording and/or determining a trajectory solely of the application point during a movement of the leg; and
  a model-generating means for creating, from data thus obtained, a kinematic model of the length conditions, the position and/or the radius of movement of at least parts of lower extremities of the patient, the apparatus with said model-generating means programmed to:
  compare coordinate pairs or coordinate triplets with a model function in a form of a coordinate equation, and in a context of a curve-fitting, a position of a rotation point and/or a length between the application point and the rotation point, and an angle between two points on the trajectory and the rotation point being determined;
  use the coordinate equation $$\frac{(Y_n - M_Y(Y_H))^2}{L_0^2} + \frac{(Z_n - M_Z(Z_H))^2}{(L_0 \pm \Delta L)^2} = 1$$

for an ellipse as the model function, where $L_0 \pm \Delta L$ represents a possible displacement of the position of the rotation point during the movement;
  use as a parameter for a center point of the ellipse, a function according to the position of the rotation point; and
  use as a semi-major axis of the ellipse, the length between the application point and the rotation point.

15. The apparatus according to claim 14, wherein said measuring device has at least two sensors for determining an angle position of a shaft of said electric motor and/or of said eccentrics.

16. The apparatus according to claim 14, further comprising a control module for controlling planned rehabilitation movements of at least joints, muscles and tendons of legs of the bedridden patient by means of said at least one knee module, wherein said control module is configured to determine, from patient-specific data generated from the kinematic model, trajectories for rehabilitation movements of the leg of the patient with respect to the application point, and, on a basis of the trajectories, to control said at least one knee module.

17. The apparatus according to claim 14, wherein said at least one knee module has:
- at least one knee orthosis for receiving a knee joint of the bedridden patient;
- a connection element connected to said at least one knee orthosis;
- an extension arm on which said connection element is secured; and
- a mechanical device driven by means of said control module, wherein said mechanical device introduces a defined force into said at least one knee orthosis, via said extension arm and said connection element, in such a way that the joints, the muscles and the tendons of the leg perform planned rehabilitation movements via the application point.

18. The apparatus according to claim 17, wherein said rehabilitation mechanism contains:
- at least one angle sensor which monitors an angle adopted by said connection element to said at least one knee orthosis and/or to said extension arm; and/or
- a force sensor which monitors the force introduced into said at least one knee orthosis via said extension arm and said connection element.

\* \* \* \* \*